United States Patent [19]

Mizushima et al.

[11] Patent Number: 5,372,814
[45] Date of Patent: Dec. 13, 1994

[54] STEROL DERIVATIVE, PROCESS FOR PRODUCING THE SAME AND DERMATOLOGIC EXTERNAL PREPARATION

[75] Inventors: Hiromoto Mizushima, Wakayama; Junichi Fukasawa, Kanagawa, both of Japan

[73] Assignee: Kao Corporation, Tokyo, Japan

[21] Appl. No.: 12,746

[22] Filed: Feb. 3, 1993

[30] Foreign Application Priority Data

Feb. 5, 1992 [JP] Japan .................. 4-019942
Apr. 17, 1992 [JP] Japan .................. 4-098001

[51] Int. Cl.$^5$ ............................... A61K 6/00
[52] U.S. Cl. .................. 424/401; 552/540; 560/194
[58] Field of Search ............. 424/401; 552/540; 560/194

[56] References Cited

U.S. PATENT DOCUMENTS 4,393,044 7/1983 Takada et al. ............. 424/59

FOREIGN PATENT DOCUMENTS 0028456 9/1980 European Pat. Off. .
0028457 9/1980 European Pat. Off. .
0134954 7/1984 European Pat. Off. .
0227641 2/1988 European Pat. Off. .
0443592 2/1991 European Pat. Off. .
9001323 2/1990 WIPO .

OTHER PUBLICATIONS

B. Bonnekoh et al, In Vivo, vol. 5, No. 3, pp. 227–232, 1991.
Chemical Abstracts, vol. 83, No. 13, p. 595, Sep. 29, 1975.
Patent Abstracts of Japan, vol. 13, No. 174 (C–589) (3522), Apr. 25, 1989.

*Primary Examiner*—Paul J. Killos
*Attorney, Agent, or Firm*—Birch, Stewart, Kolasch & Birch

[57] ABSTRACT

A sterol derivative represented by the general formulas (I) or (II) which is widely usable as the external base for the skin, emulsifier, etc., for cosmetics, toiletries, medicines, etc., since they have an excellent effect of remedying the chaps of the skin, are capable of stabilizing the lamellar liquid crystal structure and have an excellent surface-activating effect:

$$R^1-\overset{O}{\underset{\|}{C}}-R^2-\overset{O}{\underset{\|}{C}}-OM \quad (I)$$

and $$(R^1-\overset{O}{\underset{\|}{C}}-R^2-\overset{O}{\underset{\|}{C}}-O)_2L \quad (II)$$

wherein:
$R^1$ represents a residue remaining after removing the hydrogen atom from the hydroxyl group of a sterol having one hydroxyl group,
$R^2$ represents a group of the formula:

$$-\underset{\underset{R^3}{|}}{CH}-CH_2- \text{ or } -CH_2-\underset{\underset{R^3}{|}}{CH}-$$

(in which $R^3$ represents an alkenyl or alkyl group having 6 to 20 carbon atoms),
M represents a hydrogen atom, alkali metal, etc., and L represents an alkaline earth metal.

A dermatologic external preparation having an excellent effect of remedying the chaps of the skin, and being capable of stabilizing the lamellar liquid crystal structure, which comprises a ceramide and/or a structural analog of a ceramide, and the above-described sterol derivative.

24 Claims, 3 Drawing Sheets

STEROL DERIVATIVE, PROCESS FOR PRODUCING THE SAME AND DERMATOLOGIC EXTERNAL PREPARATION

BACKGROUND OF THE INVENTION

1. Field of the Invention

The present invention relates to a novel sterol derivative having an effect of remedying chapped skin and a surface-activating effect, as well as, being useful as a base for cosmetics, toiletries or medicines.

The present invention also relates to a process for producing said novel sterol derivatives.

Further, the present invention relates to a dermatologic external preparation, more particularly, to a dermatologic external preparation whereby the water retention capability of the corneal layer is elevated and thus the chapped skin can be remedied.

2. Description of the Related Art

It has been known that moisture contained in the corneal layer is important for moistening and softening the skin. It is thought that water soluble components contained in the corneal layer, namely, free amino acids, organic acids, urea or inorganic ions contribute to the retention of moisture. Either one of these substances or a combination thereof has been used in medicinal dermatologic external preparations or cosmetics in order to remedy or prevent chapped skin. Separately, a number of humectants having strong affinities for water have been developed and employed for similar purposes as those described above.

It has been recently found that a lipid present in an inter-corneal-cellular space forms a lamellar structure in the presence of water to play an important role in retaining moisture of the corneal layer [see G. Imokawa, M. Hattori, J. Invest. Dermatol., 84, 282 (1985)].

Further it has been elucidated that among the intercellular lipids, ceramides and cholesterol esters, in particular, have an improved effect of remedying chapped skin when they are applied on the skin [see G. Imokawa et al., Arch. Dermatol. Res., 281, 45 (1989)].

In addition, it has been attempted to moisten and to soften the skin with an artificial intercellular lipid comprising a substance analogous to the inter-corneal-cellular lipid to obtain a relatively excellent improving effect [see Genji Imokawa, Fragrance Journal, 4, 26 (1990), and Genji Imokawa, et al., "Kinosei Keshohin (Functional Cosmetics)", 235, published by CMC (1990)].

However, the application of humectants such as water soluble components contained in the corneal layer to the skin is effective merely in supplying moisture to the corneal layer on the skin corneal layer, and the effect is only temporary. It is, therefore, impossible to fundamentally improve the water retention capability of the corneal layer to thereby essentially prevent or treat chapped skin thereby.

On the other hand, although the water retention function of tile corneal layer can be improved and the skin can be prevented from chapping or chapped skin can be remedied to some extent by applying the artificial intercellular lipid to the skin, no healthy skin can be completely recovered to the previous level, so that the effect of the artificial intercellular lipld is not yet satisfactory.

Under these conditions, it has been eargerly demanded to develop a base for an external preparation for the skin and a dermatologic external preparation which are capable of fundamentally improving the water retention capacity of the corneal layer of chapped skin to restore the function of the skin to a level equal or superior to that of the healthy living body and also moistening and softening the skin.

DISCLOSURE OF THE INVENTION

Summary of the Invention

Under these circumstances, the present inventors have noted the intermolecular effect of the inter-corneal-cellular lipid components to conduct extensive investigations for the purpose of solving the above problem. As a result, they have found that the intercellular lipid components including the ceramides form a lamellar liquid crystal structure in the presence of water when it is applied to the chapped skin, whereby a remarkable effect of remedying chapped skin can be obtained.

Therefore, the inventors have studied to find compounds which can form lamellar liquid crystals by themselves without any other substance, or which can stabilize the lamellar liquid crystal structure formed by the intercellular lipid. As a result, the inventors have found that a sterol derivative of the general formulas (I) or (II) given below per se has remarkable effects of remedying chapped skin and stabilizing the lamellar liquid crystal structure formed by the intercellular lipid and that surprisingly, some of the sterol derivatives of the general formulas (I) or (II) are capable of forming lamellar liquid crystals by themselves without any other substance and when they are used as an emulsifier, they exhibit such a high surface-activating capacity that they can stabilize a W/O emulsion. Further, they have successfully found that a dermatologic external preparation, which comprises component (A) consisting of a ceramide represented by the following general formula (1) and/or a structural analog of ceramide represented by the following general formula (2) and component (B) consisting of a sterol derivative, that is, a monoester of a cholesterol with a dicarboxylic acid, represented by the following general formulas (V) or (VI), are capable of fundamentally improving the water retention capacity of the corneal layer of the chapped skin to restore the function of the skin to a level equal or superior to that of the healthy living body and also moistening and softening the skin.

The present invention has been completed on the basis of these findings.

Thus the present invention provides a sterol derivative represented by the following general formulas (I) or (II):

(I)

wherein

R$^1$ represents a residue remaining after removing the hydrogen atom from the hydroxyl group of a natural sterol having one hydroxyl group or a hydrogenation product thereof, R$^2$ represents a group of the formulas:

(in which R³ represents a straight-chain or branched alkenyl or alkyl group having 6 to 20 carbon atoms), and M represents a hydrogen atom, alkali metal, ammonium, alkanolammonium having 2 to 9 carbon atoms in total, alkylammonium or alkenylammonium having 1 to 22 carbon atoms in total, pyridinium substituted by an alkyl or alkenyl group having 1 to 18 carbon atoms, or a basic amino acid, and $$(R^1-\overset{O}{\underset{\|}{C}}-R^2-\overset{O}{\underset{\|}{C}}-O)_2 L \qquad (II)$$

wherein
R¹ represents a residue remaining after removing the hydrogen atom from the hydroxyl group of a natural sterol having one hydroxyl group or a hydrogenation product thereof,
R² represents a group of the formulas:

(in which R³ represents a straight-chain or branched alkenyl or alkyl group having 6 to 20 carbon atoms), and
L represents an alkaline earth metal.

The sterol derivative according to the present invention includes:
(1) those represented by the general formulas (I) or (II) wherein the natural sterol is cholesterol, stigmasterol, sitosterol, lanosterol or ergosterol.
(2) those represented by the general formulas (I) or (II) wherein R¹ and R³ represent a residue remaining after removing the hydrogen atom from the hydroxyl group of the cholesterol and a straight-chain alkenyl or alkyl group having 6 to 20 carbon atoms, respectively.
(3) those represented by the following general formula (III):

$$R^4-\overset{O}{\underset{\|}{C}}-R^5-\overset{O}{\underset{\|}{C}}-OH \qquad (III)$$

wherein
R⁴ represents a residue remaining after removing the hydrogen atom from the hydroxyl group of a natural sterol having one hydroxyl group, and
R⁵ represents a group of the formula:

(in which R⁶ represents a straight-chain or branched alkenyl or alkyl group having 6 to 18 carbon atoms).
(4) a mixture of two sterol derivatives which are represented by the general formulas (I) or (II), wherein the two sterol derivatives are different from each other with respect to only R² and one has a group of the formula:

in which R³ represents a straight-chain or branched alkenyl or alkyl group having 6 to 20 carbon atoms) as R², and another has a group of the formula:

(in which R³ represents a straight-chain or branched alkenyl or alkyl group having 6 to 20 carbon atoms) as R².
(5) a mixture of two sterol derivatives which are represented by tile general formula (IV):

$$R^4-\overset{O}{\underset{\|}{C}}-R^7-\overset{O}{\underset{\|}{C}}-OH \qquad (IV)$$

wherein
R⁴ represents a residue remaining after removing the hydrogen atom from the hydroxyl group of a natural sterol having one hydroxyl group, and
R⁷ represents a group of the formulas:

(in which R⁶ represents a straight-chain or branched alkenyl or alkyl group having 6 to 18 carbon atoms), with the proviso that the two sterol derivatives are different from each other with respect to only R⁷, and that one has a group of the formula:

(in which R⁶ represents a straight-chain or branched alkenyl or alkyl group having 6 to 18 carbon atoms) as R⁷ and another has a group of the formula:

(in which R⁶ represents a straight-chain or branched alkenyl or alkyl group having 6 to 18 carbon atoms) as R⁷.

The sterol derivatives of the present invention are strictly differentiated from esters of a sterol with a monocarboxylic acid heretofore used as a base for an external preparation for the skin for the purpose of remedying chapped skin (see U.S. Pat. No. 4,309,448 (patented on Jan. 5, 1982, Kao Soap K.K.), since the former per se have a remarkable effect of remedying chapped skin, are capable of stabilizing the lamellar liquid crystal structure formed by the inter-corneal-cellular lipid in the presence of water, and are usable as an emulsifier in virtue of their excellent surface-activating effect.

The present invention also provides a process for producing the sterol derivative according to the present invention, which comprises reacting a natural sterol having one hydroxyl group or a hydrogenation product thereof with an alkenylsuccinic anhydride or an alkylsuccinic anhydride.

Further, the present invention also provides a process for producing the mixture of two sterol derivatives according to the present invention, which comprises reacting a natural sterol having one hydroxyl group or a hydrogenation product thereof with an alkenylsuccinic anhydride or an alkylsuccinic anhydride.

The above reaction is preferably conducted in the presence of an organic solvent substantially free from water and alcohols or in the presence of a reaction catalyst such as an acidic substance.

In the above process, the neutralization/counter ion exchange step is preferably conducted after the reaction.

Furthermore, the present invention provides a dermatologic external preparation comprising the following components (A) and (B):

(A) one or more compounds selected from the group consisting of ceramides represented by the following general formula (1) and structural analogs of ceramides represented by the following general formula (2):

(1)

wherein $R^a$ and $R^b$ each represent a straight-chain or branched, saturated or unsaturated hydrocarbon group having 8 to 26 carbon atoms which may be optionally substituted by one or more hydroxyl groups, and

(2)

wherein $R^c$ represents a straight-chain or branched, saturated or unsaturated hydrocarbon group having 10 to 26 carbon atoms, and $R^d$ represents a straight-chain or branched, saturated or unsaturated hydrocarbon group having 9 to 25 carbon atoms, and (B) one or more sterol derivatives represented by the following general formulas (V) or (VI):

(V)

wherein
$R^1$ represents a residue remaining after removing the hydrogen atom from the hydroxyl group of a natural sterol having one hydroxyl group or a hydrogenation product thereof,
$R^8$ represents a group of the formulas: —$(CH_2)_n$— in which n is an integer of 2 to 10), —CH=CH—, (in which $R^9$ represents a straight-chain or branched alkenyl or alkyl group having 3 to 20 carbon atoms), and M represents a hydrogen atom, alkali metal, ammonium, alkanolammonium having 2 to 9 carbon atoms in total, alkylammonium or alkenylammonium having 1 to 22 carbon atoms in total, pyridinium substituted by an alkyl or alkenyl group having 1 to 18 carbon atoms, or basic amino acid, and

(VI)

wherein
$R^1$ represents a residue remaining after removing the hydrogen atom from the hydroxyl group of a natural sterol having one hydroxyl group or a hydrogenation product thereof,
$R^8$ represents a group of the formulas: —$(CH_2)_n$— (in which n is an integer or 2 to 10), —CH=CH—, (in which $R^9$ represents a straight-chain or branched alkenyl or alkyl group having 3 to 20 carbon atoms), and L represents an alkaline earth metal.

The component (B) is preferably one member selected form the group consisting of sterol derivatives according to the present invention, one member selected form the group consisting of sterol derivatives represented by the following general formula (VII):

(VII)

wherein
$R^4$ represents a residue remaining after removing the hydrogen atom from the hydroxyl group of a natural sterol having one hydroxyl group, and $R^{10}$ represents a group of the formulas: —$(CH_2)_n$— (in which n is an integer of 2 to 10), —CH=CH— or

(in which $R^{11}$ represents a straight-chain or branched alkenyl or alkyl group having 3 to 18 carbon atoms), one member selected form the group consisting of sterol derivatives represented by the following general formula (VIII):

(VIII)

wherein
$R^4$ represents a residue remaining after removing the hydrogen atom from the hydroxyl group of a natural sterol having one hydroxyl group, and $R^{12}$ represents a group of the formulas: —$(CH_2)_n$— (in which n is an integer of 2 to 10) or —CH=CH—, and a mixture of two sterol derivatives represented by the following general formulas (IX) and (X):

(IX)

and

(X)

wherein
R⁴ represents a residue remaining after removing the hydrogen atom from the hydroxyl group of a natural sterol having one hydroxyl group, and R¹¹ represents a straight-chain or branched alkenyl or alkyl group having 3 to 18 carbon atoms), with the proviso that R⁴ in the general formula (IX) and R⁴ in the general formula (X) are same each other and that R¹¹ in the general formula (IX) and R⁴ in the general formula (X) are same each other, or one member selected from the group consisting of the mixture of two sterol derivatives which are represented by the general formulas (I) or (II) and which are different from each other with respect to only R², with the proviso that one has a group of the formula:

(in which R³ represents a straight-chain or branched alkenyl or alkyl group having 6 to 20 carbon atoms) as R², and another has a group of the formula:

(in which R³ represents a straight-chain or branched alkenyl or alkyl group having 6 to 20 carbon atoms) as R².

The dermatologic external preparation has preferably the compositional ratio of the component (A) to component (B) being from 95:5 to 5:95 by weight.

The dermatologic external preparation includes one which is an emulsifiied type and which has the total amount of the components (A) and (B) ranging from 0.01 to 60% by weight based on the whole preparation, and one which is an oily type and which has the total amount of the components (A) and (B) ranging from 1 to 90% by weight based on the whole preparation.

The dermatologic external preparation is a medicinal one, a cosmetic, etc.

Further, the scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the sterol derivatives of the general formulas (I), (II), (V) or (VI), R¹ represents a residue remaining after removing the hydrogen atom from the hydroxyl group of a natural sterol having one hydroxyl group (such as cholesterol, stigmasterol, sitosterol, lanosterol or ergosterol) or a hydrogenation product thereof. Among them, R¹ is preferably a cholesterol residue. R⁴ in the general formulas (III), (IV), (VII), (VIII), (IX) or (X) represents a residue remaining after removing the hydrogen atom from the hydroxyl group of a natural sterol having one hydroxyl group.

In the sterol derivatives of the general formulas (I) or (II), R³ represents a straight-chain or branched alkenyl or alkyl group having 6 to 20 carbon atoms, such as straight-chain or branched 2-hexenyl, 2-octenyl, 2-decenyl, 2-dodecenyl, 2-tetradecenyl, 2-hexadecenyl, 2-octadecenyl, 2-eicosenyl, hexyl, octyl, decyl, dodecyl, tetradecyl, hexadecyl, octadecyl and eicosyl groups, among which preferred are 2-tetradecenyl, 2-hexadecenyl, 2-octadecenyl, 2-eicocenyl, tetradecyl, hexadecyl, octadecyl and eicosyl groups.

R⁶ in the general formulas (III) or (IV) represents a straight-chain or branched alkenyl or alkyl group having 6 to 18 carbon atoms. Specific examples thereof include those having 3 to 18 carbon atoms among those described above with respect to R³.

R⁹ in the general formulas (V) or (VI) represents a straight-chain or branched alkenyl or alkyl group having 3 to 20 carbon atoms, such as propyl, isopropyl, n-butyl, tert-butyl, pentyl, hexyl, octyl, nonyl, decyl, dodecyl, undecyl, tridecyl, tetradecyl, pentadecyl, hexadecyl, heptadecyl, octadecyl, propenyl, butenyl, pentenyl, hexenyl, heptenyl, octenyl, nonenyl, decenyl, dodecenyl, undecenyl, tridecenyl, tetradecenyl, pentadecenyl, hexadecenyl, heptadecenyl and octadecenyl groups.

R¹¹ in the general formulas (VII), (IX) or (X) represents a straight-chain or branched alkenyl or alkyl group having 3 to 18 carbon atoms. Specific examples thereof include those having 3 to 18 carbon atoms among those described above with respect to R⁹.

Specific examples of the —(CH₂)ₙ— represented by R⁸ in the general formulas (V) or (VI), R¹⁰ in the general formula (VII) and R¹² in the general formula (VIII) include ethylene, propylene, butylene, pentamethylene, hexamethylene, heptamethylene, octamethylene, nonamethylene and decamethylene groups, among which ethylene, trimethylene and propylene groups are particularly preferable.

M in the general formulas (I) or (V) represents a hydrogen atom, alkali metal, ammonium, alkanolammonium having 2 to 9 carbon atoms in total, alkylammonium or alkenylammonium having 1 to 22 carbon atoms in total, pyridinium substituted by an alkyl or alkenyl group having 1 to 18 carbon atoms, or basic amino acid. Specific examples thereof include H₃N⁺(CH₂)₃OH, H₂N⁺(C₂H₆OH)₂, HN⁺(C₂H₆OH)₃, CH₃(CH₂)₁₁N⁺H₃ and CH₃(CH₂)₁₁N⁺H(CH₃)₂. L in the general formulas (II) or (VI) represents an alkaline earth metal.

The sterol derivatives of the present invention are widely usable in the production of cosmetics, toiletries or medicines, taking advantage of their effects of remedying the chapped skin and surface activation.

The sterol derivatives represented by the general formulas (I) and (II) [hereinafter referred to as "sterol derivatives (I) and (II)"] and the mixture of two sterol derivatives provided by the present invention are obtained by reacting a sterol with an alkenylsuccinic anhydride or an alkylsuccinic anhydride and, if necessary, neutralizing the reaction product with an alkaline substance. Those having no unsaturated double bond in the $R^1$ and $R^3$ groups can be obtained also by reacting a sterol with an alkenylsuccinic anhydride or an alkylsuccinic anhydride and hydrogenating the reaction product by an ordinary method wherein, for example, a noble metal catalyst is used.

After extensive investigations on the processes for synthesizing the sterol derivatives (I) and (II) and the mixture of two sterol derivatives provided by the present invention, the inventors have found that when a sterol is reacted with an alkenylsuccinic anhydride or an alkylsuccinic anhydride, preferably in the presence of an acidic substance or an alkaline substance, in a solvent substantially free from water and alcohols, a corresponding sterol derivative or a mixture of two corresponding sterol derivative is obtained in a high yield. The inventors have completed the process of the present invention on the basis of this finding. An example of this reaction can be specifically illustrated as follows:

wherein $R^{2'}$

The solvents usable for the reaction of the present invention are organic solvents substantially free from water and alcohols, such as benzene, toluene, xylene, dimethylformamlde (DMF), dimethyl sulfoxide (DMSO), dioxane, 1,2-dichloroethane, ethylene glycol dimethyl ether and ethylene glycol diethyl ether, among which toluene and xylene are desirable, since the starting sterol compound is easily soluble therein, and they are stable and not easily colored even in the presence of the acidic or alkaline substance used as the reaction catalyst. Examples of the acidic substances usable as the reaction catalyst include p-toluenesulfonic acid (PTS), formic acid, acetic acid, hydrochloric acid and sulfurlc acid, among which p-toluenesulfonic acid (PTS) which difficultly colors the product is desirable. Examples of the alkaline substances usable as the reaction catalyst include pyridine, triethylamine, potassium hydroxide and sodium hydroxide, among which pyridlne and triethylamine are preferred from the viewpoint of the solubility in a solvent.

Although the reaction can be conducted also in the absence of any solvent or reaction catalyst comprising an acidic or alkaline substance, the use of a solvent is preferred, since when the reaction is conducted in the absence of any solvent, a reaction temperature of as high as the melting point of the sterol or above is inevitable to accelerate side reactions to form a diester by the esterification of both carbonyl groups of the alkenylsuccinic anhydride or alkylsuccinie anhydrideused as the reactant. Further, the use of an acidic substance or an alkaline substance as the reaction catalyst is preferred, since when the reaction is conducted in the absence of such a reaction catalyst, the reaction velocity is so low that an extremely high reaction temperature or long reaction time is necessitated to accelerate the side reactions to form a diester or the like as in the reaction conducted in the absence of any solvent.

As for the reaction catalyst, an acidic substance is preferable to an alkaline substance for preventing the coloration. The amount of the alkenylsuccinic anhydride, alkylsuccinic anhydride or a mixture of them used as the reactant is preferably 1 to 1.5 mol per mole of the sterol. The reaction temperature is preferably 40° to 180° C., still preferably 60° to 150° C. When the reaction temperature exceeds 180° C., side reactions such as formation of diester becomes seriously unfavorable. A reaction time of 30 min to 20 h is sufficient, though it varies depending on the reaction temperature and the amount of the acidic or alkaline substance. The amount of the acidic substance is about 0.01 to 10% by weight, preferably 0.1 to 2% by weight, based on the sterol used as the reactant. When the alkaline substance is used as the reaction catalyst, it is used in an amount of about 0.1 to 2.0 mol, preferably 1.0 to 1.5 mol, per mole of the alkenylsuccinic anhydride, alkylsuccinic anhydride or a mixture of them used as the reactant.

The intended sterol derivative (I) or (II) can be obtained by appropriately selecting the amounts of the solvent, the acidic or alkaline substance used as the reaction catalyst and the alkenylsuccinic anhydride, alkylsuccinic anhydride or a mixture of them, reaction time and reaction temperature as described above. When the alkaline substance is used as the reaction catalyst, the sterol derivative (I) or (II) thus obtained is of a carboxylic acid type or alkali-neutralized salt type or inthe form of a mixture of these two types depending on the amount of the alkaline substance used.

A desired group M in the general formula (I) or a desired group L in the general formula (II) can be obtained as follows, if necessary: (A) the alkaline substance is added to obtain a completely alkali-neutralized salt, (B) the acid substance is added to obtain a complete carboxylic acid type, (C) further the alkaline substance is added to the carboxylic acid-type steroi derivative to convert it into another alkali-neutralized salt, or (D) when the acid substance is added or when neither acidic substance nor alkaline substance is added, the sterol derivative obtained after the completion of the reaction is in the acid form, which can be converted, if necessary, into a completely alkali-neutralized salt type or a mixture of the alkali-neutralized salt type and the acid type by the addition of the alkaline substance [these steps (A) through (D) will be refereed to briefly as the "neutralization/counter ion exchange step"].

Examples of the alkaline substances usable in the neutralization/counter ion exchange step include inorganic alkalis such as sodium hydroxide, potassium hydroxide, lithium hydroxide, barium hydroxide, sodium hydrogencarbonate, sodium carbonate and potassium carbonate; monoethanolamine, diethanolamine, triethanolamine, decylamine, dodecylamine, tetradecylamlne, hexadecylamine, octadecylamine, and basic amino acids. They can be used in the form of a solution thereof in water, an organic solvent or a mixture of them. Examples of the acidic substances usable in the neutralization/counter ion exchange step include hydrochloric, sulfuric, formic, acetic and propionic acids. They can be used in the form of a solution thereof in water, an organic solvent or a mixture of them.

In the neutralization/counter ion exchange step, it will suffice when the above alkaline or acidic substance usable in the neutralization/counter ion exchange step or its solution in water, an organic solvent or a mixture of them is stirred together with the sterol derivatives (I) or (II) obtained by the above reaction at a temperature of 80° C. or below for about 1 hour.

The solvent contained in a mixture containing the sterol derivatives (I) or (II) thus obtained is distilled off by heating under reduced pressure (solvent-removing step). Then the remaining inorganic and organic salts can be removed by electrodialysis, adsorption with an ion exchange resin or adsorbent, washing with water or recrystallization (desalting step). If necessary, a further purification by column chromatography or the like (purification step) is also possible. Depending on the use of the product, the above neutralization/counter ion exchange step, solvent-removing step, desalting step and purification step can be dispensed with.

The ceramide as the component (A) to be used in the present invention is a well-known compound which is represented by the above general formula (1). Examples of the groups represented by $R^a$ and $R^b$ in the general formula (1) include octyl, nonyl, decyl, dodecyl, undecyl, tridecyl, tetradecyl, pentadecyl, hexadecyl, heDtadecyl, octadecyl, nonadecyl, eicosyl, heneicosyl, docosyl, tricosyl, tetracosyl, pentacosyl, hexacosyl, nonenyl, decenyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadlenyl, 2-hexyldecyl, 2-octylundecyl and 2-decyltetradecyl groups.

The structural analogs of ceramides represented by the above general formula (2) as the component (A) can be produced in accordance with known methods [see, for example, Pol. J. Chem., 52, 1059 (1978), ibid., 52, 1283 (1978), Japanese Patent Publication-A Nos. 117421/1979 (Sep. 12, 1979), 144308/1979 (Nov. 10, 1979), 147937/1979 (Nov. 19, 1979) and 216852/1988 (Sep. 9, 1988) and European Patent Publication-A No. 227994 (Jul. 8, 1987)]. More specifically, they can be produced by reacting a compound (4) obtained from glycidyl ether and ethanolamine with a fatty acid methyl ester in accordance with the following reaction scheme:

(2)

wherein $R^c$ represents a straight-chain or branched, saturated or unsaturated hydrocarbon group having 10 to 26 carbon atoms, and $R^d$ represents a straight-chain or branched, saturated or unsaturated hydrocarbon group having 9 to 25 carbon atoms.

Examples of the group represented by $R^c$ in the general formula (2) include those having from 10 to 26 carbon atoms selected from among the ones cited above regarding $R^a$ and $R^b$, while examples of the group represented by $R^d$ therein include those having from 9 to 25 carbon atoms selected from among the ones cited above regarding $R^a$ and $R^b$.

Either one of these ceramides and structural analogs thereof or a mixture comprising two or more of the same may be used as the component (A).

The sterol derivatives, that is, monoesters of cholesterols with dicarboxylic acids to be used as the component (B) in the present invention are represented by the above general formulas (V) or (VI).

Well-known monoesters may be used as the component (B), and examples thereof include cholesterol hemisuccinate, cholesterol hemiglutarate and cholesterol hemimaleate. The sterol derivatives represented by the general formulas (I) or (II) are preferably used as the component (B). In general, the mixture of two sterol derivatives represented by the general formulas (I) or (II), with the proviso that the two sterol derivatives are different from each other with respect to only $R^2$, and that one has a group of the formula:

(in which $R^3$ represents a straight-chain or branched alkenyl or alkyl group having 6 to 20 carbon atoms) as $R^2$, and another has a group of the formula:

(in which $R^3$ represents a straight-chain or branched alkenyl or alkyl group having 6 to 20 carbon atoms) as $R^2$ is used as the component (B).

Either one of these components (B) or a mixture comprising two or more of them may be used.

The compositional ratio of the component (A) to the component (B) in the dermatologic external preparation according to the present invention may preferably range from 95:5 to 5:95 by weight. These components may be preferably blended to other components by mixing these components at the ratio as specified above, melting the mixture by heating, then cooling it and adding the pasty material thus obtained to other components.

The content of the mixture of the components (A) and (B) in the dermatologic external preparation of the present invention is not particularly restricted. In the case of a common emulsified dermatologic external preparation, this content preferably ranges from 0.01 to 60% by weight (hereinafter simply expressed as %), in particular, from 0.1 to 30% based on the whole preparation. In the case of an oily dermatologic external preparation containing a liquid hydrocarbon such as squalane as a base, the content of the mixture preferably ranges from 1 to 90%, still preferably from 5 to 50%.

The dermatologic external preparation according to the present invention may be roughly classified into medicinal dermatologic external preparations and cosmetics depending on the usage form.

Examples of the medicinal dermatologic external preparations include various ointments containing drug ingredients. These ointments may be any of those containing an oily base and those containing an oil-in-water or water-in-oil emulsion base. Any oily base may be selected without restriction, and examples thereof include vegetable oils, animal oils, synthetic oils, fatty acids and natural and synthetic glycerides. The drug ingredients may be selected without restriction and use may be made of, for example, analgesic/antiinflammatory agents, antipruritic agents, bactericides/disinfections, astringents, emollients and hormone preparations which may be suitably selected according to need.

When used as a cosmetic, the preparation may contain the essential components of the present invention together with components which are arbitrarily selected and combined from among those commonly employed in the art, for example, oils, humectants, UV absorbers, alcohols, chelating agents, pH regulators, preservatives, thickeners, colorants and perfumes.

The cosmetic may be formulated into various form, namely skin cosmetics such as water-in-oil or oil-in-water emulsion cosmetics, creams, cosmetic emulsions, cosmetic lotions, oily cosmetics, lipsticks, foundations, detergents for skill, hair tonics, hair styling agents, hair nourishments and trichogens.

Although the detailed mechanism of the function of the mixture of the components (A) and (B) of the dermatologic external preparation according to the present invention has not yet been completely clarified, it is conceivable that this mixture may construct a lipid double layer together with water in an inter-corneal-cellular space to thereby exert a function of retaining the moisture contained in the corneal layer.

The sterol derivatives (I) and (II) of the present invention are widely usable as the external base for the skin, emulsifier, etc., for cosmetics, toiletries, medicines, etc., since they have an excellent effect of remedying chapped skin when they per se are applied to the skin, are capable of stabilizing the lamellar liquid crystal structure formed by the inter-corneal-cellular lipid in the presence of water and have an excellent surface-activating effect.

The dermatologic external preparation of the present invention, which contains a mixture of the components (A) and (B), can exert excellent effects of remedying and preventing chapped skin.

EXAMPLES

The following Examples will further illustrate the present invention, which by no means limit the invention.

EXAMPLE 1

109.1 g (282 mmol) of cholesterol was fed into a 500-ml reaction vessel provided with a thermometer and a stirrer and then heated to 160° C. on an oil bath in a nitrogen gas stream to melt cholesterol. 90.9 g (282 mmol) of n-hexadecenylsuccinlc anhydride was added to the vessel and the resultant mixture was heated at 160° C. under stirring for 10 min, cooled to 130° C., and stirred for additional 1 h. The reaction mixture was cooled to room temperature to obtain 200 g of a light yellow, viscous paste. This product was purified by silica gel column chromatography (mobile phase: hexane/ethyl acetate=4/1) to obtain 178.4 g (yield: 89.2%) of monocholesteryln-hexadecenylsuccinate in the form of a colorless, translucent paste.

The found and calculated acid values, saponification values and hydroxyl values of the monocholesteryl n-hexadecenylsuccinate thus obtained are given in Table 1.

TABLE 1

|  | Acid value | Saponification value | Hydroxyl value |
|---|---|---|---|
| Found | 77.9 | 157.6 | 0.2 |
| Calcd. | 79.2 | 158.4 | 0 |

Figure 1:
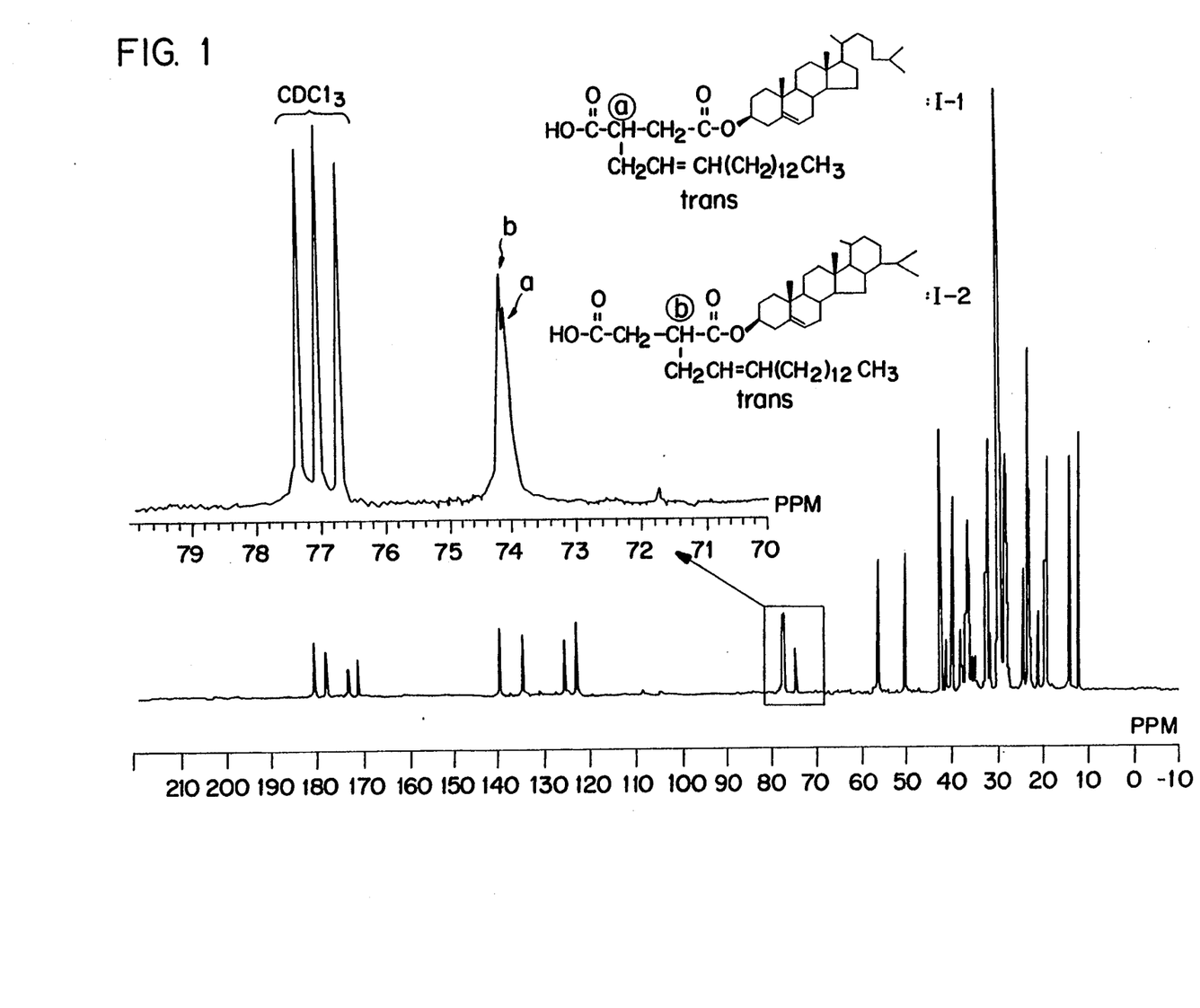
FIG. 1 shows the $^{13}$C-NMR spectrum of the compound obtained in Example 1.

The IR spectrum and $^1$H-NMR spectrum of the obtained monocholesteryl n-hexadecenylsuccinate were as given below and the elementary analysis values thereof were as given in Table 2. The $^{13}$C-NMR spectrum is given in FIG. 1. It was apparent from FIG. 1 that the product was a mixture of two isomers (I-1 and I-2 in a weight ratio of about 1:1) having a n-hexadecenyl group in different positions of substitution.

IR spectrum (liquid film method):
2960, 2926, 2854, 1740 (C=O stretching),
1710 (C=O stretching), 1470, 1380 cm$^{-1}$ $^1$H-NMR spectrum ($\delta$, ppm) in CDCl$_3$:
a: 0.70 (s, 3H)
b: 0.75~2.40 (m. 55H)
c: 0.80 (d, 6H)
d: 0.93 (d, 3H)
e: 1.00 (s, 3H)
f: 2.40~3.0 (m, 3H)
g: 4.65 (m. 1H)
h: 5.35 ( m, 3 H)
i: 11.5 (m, 1H)

TABLE 2

| | Elementary analysis: | | |
|---|---|---|---|
| | C (%) | H (%) | O (%) |
| Found | 79.53 | 11.60 | 9.11 |
| Calcd. | 79.61 | 11.37 | 9.02 |

EXAMPLE 2

52.4 g (136 mmol) of cholesterol, 47.6 g (136 mmol) of n-octadecenylsuccinic anhydride, 0.5 g of p-toluenesulfonic acid monohydrate and 200 ml of toluene were fed into a 500-ml reaction vessel provided with a thermometer, a reflux condenser and a stirrer. The resultant mixture was heated under reflux and under stirring in a nitrogen gas stream for 3 h. 500 ml of ethyl acetate was added to the reaction mixture and the resultant mixture was washed with about 100 ml of deionized water three times by using a separatory funnel and dried over about 30 g of anhydrous sodium sulfate. Then the solvent was distilled off by heating under reduced pressure to obtain 93.2 g (yield: 93.24) of monocholesteryl n-octadecenylsuccinate in the form of a light yellow paste.

The found and calculated acid values, saponification values, hydroxyl values and water contents of the monocholesteryl n-octadecenylsuccinate thus obtained are given in Table 3.

TABLE 3

| | Acid value | Saponification value | Hydroxyl value | Water content (%) |
|---|---|---|---|---|
| Found | 75.8 | 152.6 | 0.1 | 0.07 |
| Calcd. | 76.2 | 152.3 | 0 | 0 |

Figure 2:
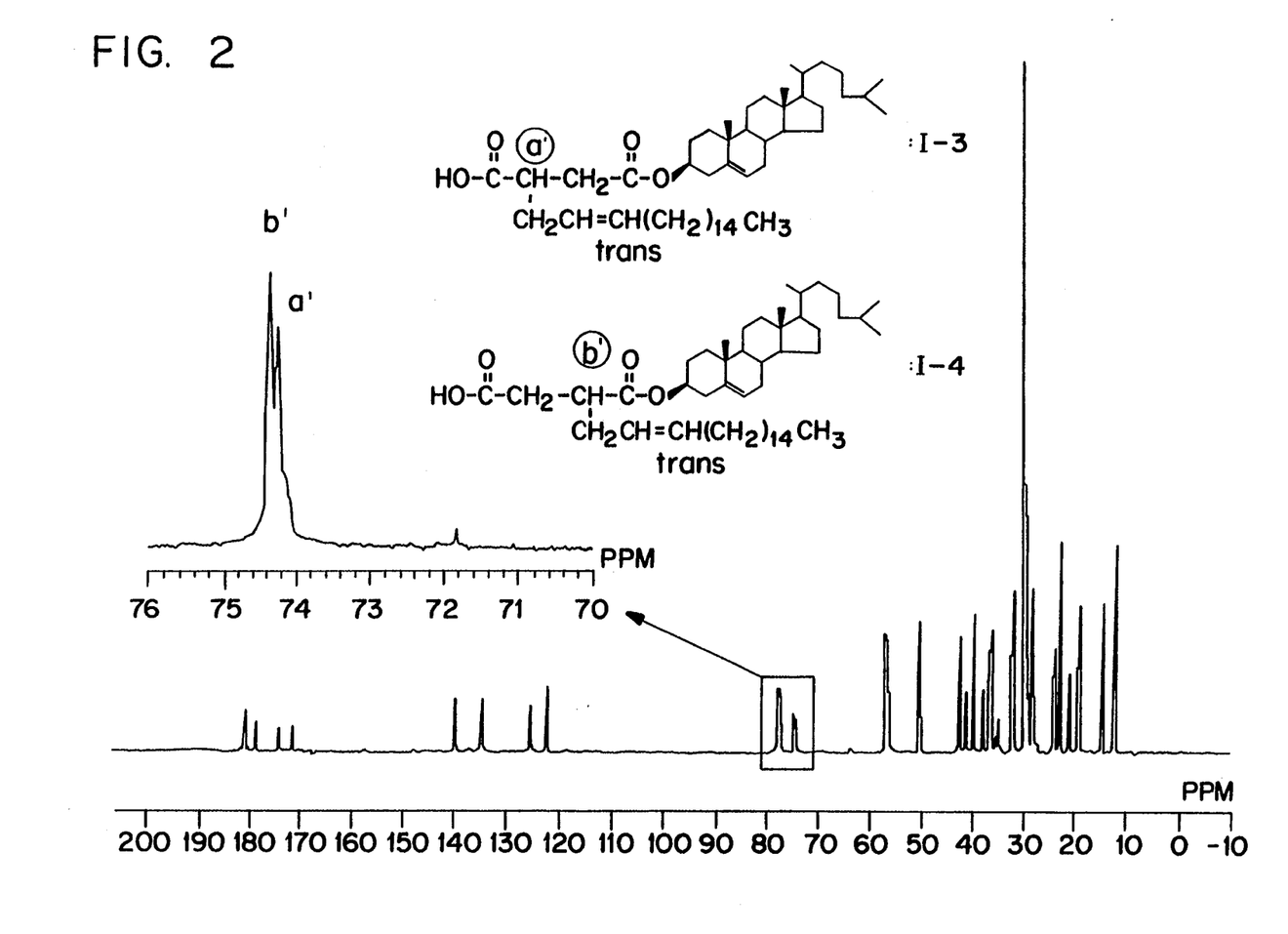
FIG. 2 shows the $^{13}$C-NMR spectrum of the compound obtained in Example 2.

The IR spectrum and $^1$H-NMR spectrum of the obtained monocholesterYl n-octadecenylsuccinate were as given below and time elementary analysis values thereof were as given in Table 4. The $^{13}$C-NMR spectrum is given in FIG. 2. It was apparent from FIG. 2 that the product was a mixture of two isomers (I-3 and I-4 in a weight ratio of about 1:1) having a n-octadecenyl group in different positions of substitution.

IR spectrum (liquid film method):
  2960, 2925, 2850, 1742 (C=O stretching),
  1713 (C=O stretching), 1460, 1380 cm$^{-1}$ $^1$H-NMR spectrum (δ, ppm) in CDCl$_3$:
  a: 0.68 (s, 3H)
  b: 0.75~2.40 (m, 59H)
  c: 0.80 (d, 6H)
  d: 0.95 (d, 3H)
  e: 1.00 (s, 3H)
  f: 2.40~3.0 (m, 3H)
  g: 4.60 (m, 1H)
  h: 5.40 (m, 3H)
  i: 11.3 (m, 1H)

TABLE 4

| | Elementary analysis: | | |
|---|---|---|---|
| | C (%) | H (%) | O (%) |
| Found | 79.65 | 11.59 | 8.76 |
| Calcd. | 79.83 | 11.48 | 8.69 |

EXAMPLE 3

59.2 g (153 mmol) of cholesterol, 40.8 g (153 mmol) of n-dodecenylsuccinic anhydride and 500 ml of pyridine were fed into a 1-l reaction vessel provided with a thermometer, a reflux condenser and a stirrer. The resultant mixture was heated under reflux and under stirring in a nitrogen gas stream for 2 h. After the completion of the reaction, excess pyridine was distilled off by heating under reduced pressure and the reaction product was neutralized with 13.8 g (223 mmol) of acetic acid. The remaining brown solid was dissolved in 500 ml of ethyl acetate, washed with about 100 ml of deionized water three times by using a separatory funnel, and dried over about 30 g of anhydrous sodium sulfate. Then the solvent was distilled off to obtain 87.3 g of a light yellow glassy substance. This product was purified by silica gel column chromatography (mobile phase: hexane/ethyl acetate=4/1) to obtain 37.9 g (yield: 37.94) of colorless, transparent, glassy monocholesteryl n-dodecenylsuccinate.

The found and calculated acid values, saponification values, hydroxyl values and water contents of the monocholesteryl n-dodecenylsuccinate thus obtained are given in Table 5.

TABLE 5

|  | Acid value | Saponification value | Hydroxyl value | Water content (%) |
|---|---|---|---|---|
| Found | 85.7 | 171.7 | 0.1 | 0.05 |
| Calcd. | 85.9 | 171.8 | 0 | 0 |

The IR spectrum and $^1$H-NMR spectrum of the obtained monocholesteryl n-dodecenylsuccinate were as given below and the elementary analysis values thereof were as given in Table 6. It was apparent from the $^{13}$C-NMR spectrum that the product was a mixture of two isomers (weight ratio: about 1:1) having a n-dodecenyl group in different positions of substitution.

IR spectrum (liquid film method):
  2955, 2920, 2850, 1740 (C=O stretching),
  1710 (C=O stretching), 1467, 1380 cm$^{-1}$ $^1$H-NMR spectrum ($\delta$, ppm) in CDCl$_3$:
  a: 0.65 (s, 3H)
  b: 0.75~2.40 (m, 47H)
  c: 0.81 (d, 6H)
  d: 0.93 (d, 3H)
  e: 1.05 (s, 3H)
  f: 2.40~3.0 (m, 3H)
  g: 4.60 (m, 1H)
  h: 5.40 (m, 3H)
  i: 11.0 (m, 1H)

EXAMPLE 4

48.5 g (68.4 mmol) of monocholesteryl n-hexadecenylsuccinate synthesized in Example 1 and 300 ml of isopropanol were fed into a 500-ml reaction vessel provided with a thermometer, a reflux condenser, a stirrer and a dropping funnel. 30 ml of an aqueous solution of 5.75 g (67.6 mmol) of sodium hydrogencarbonate was fed into the vessel through a dropping funnel for a period of about 30 min while stirring the mixture comprising monocholesteryl n-hexadecenylsuccinate and isopropanol. After the completion of the dropping, the resultant mixture was stirred at room temperature for 30 min. Water and isopropanol were distilled off from the reaction mixture by heating under reduced pressure. The remaining white solid was washed with a large amount of hexane and dried under reduced pressure to obtain 47.5 g (yield: 95.0%) of sodium monocholesteryl n-hexadecenylsuccinate.

The found and calculated acid values, saponification values and water contents of the sodium monocholesteryl n-hexadecenylsuccinate thus obtained are given in Table 7.

TABLE 7

|  | Acid value | Saponification value | Water content (%) |
|---|---|---|---|
| Found | 0.02 | 76.5 | 0.01 |
| Calcd. | 0 | 76.8 | 0 |

The IR spectrum of the obtained sodium monocholesteryl n-hexadecenylsuccinate was as given below and the elementary analysis values thereof were as given in Table 8.

IR spectrum (liquid film method):
  3406 (O-H stretching), 2926, 2854, 1731 (C=O stretching), 1575 and 1407 (C=O stretching), 1380 cm$^{-1}$

TABLE 8

|  | Elementary analysis: | | | |
|---|---|---|---|---|
|  | C (%) | H (%) | O (%) | Na (%) |
| Found | 77.40 | 10.85 | 8.62 | 3.13 |
| Calcd. | 77.21 | 10.89 | 8.75 | 3.14 |

TABLE 6

|  | Elementary analysis: | | |
|---|---|---|---|
|  | C (%) | H (%) | O (%) |
| Found | 79.01 | 11.20 | 9.79 |
| Calcd. | 79.09 | 11.11 | 9.80 |

TEST EXAMPLE 1

Figure 3:
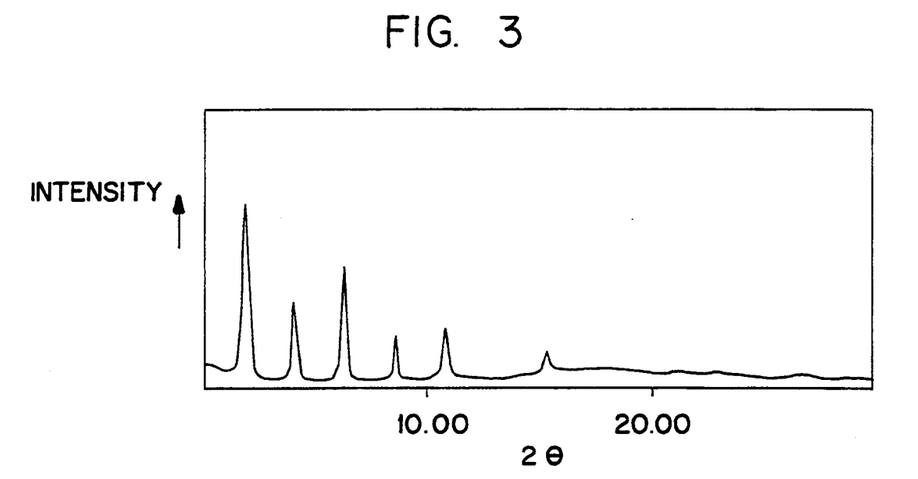
FIG. 3 is a figure showing the X-ray diffraction pattern of monocholesteryl n-hexadecenylsuccinate at room temperature.
Figure 4:
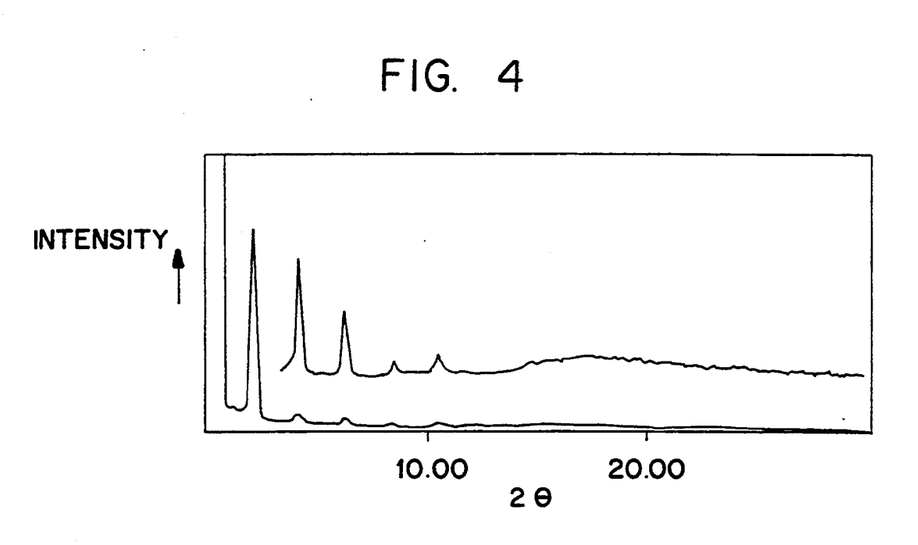
FIG. 4 is a figure showing the X-ray diffraction pattern of monocholesteryl n-octadecenylsuccinate at room temperature.

The structure (state of the phase) of each of the monocholesteryl n-hexadecenylsuccinate and monocholesteryl n-octadecenylsuccinate synthesized in Examples 1 and 2, respectively, was examined at room temperature by X-ray diffractometry. The Cu-K$\alpha$ radiation (λ=1.54 Å) was used in this study. The X-ray diffraction patterns of them are given in FIGS. 3 and 4, respectively.

It was found that monocholesteryl n-hexadecenylsuccinate (FIG. 3) formed lamellar liquid crystals at room temperature as judged from the X-ray diffraction pattern (d=43.7 Å:21.1 Å:13.8 Å:10.2 Å:8.2 Å 1:1/2:1/3:1/4:1/5) in the small-angle range and the absence of any distinct diffraction peak in the wide-angle range. It was found that also monocholesteryl n-octadecenylsuccinate (FIG. 4) was in the form of lamellar liquid crystals as judged from the X-ray diffraction pattern (d=43.0 Å:21.0 Å:14.0 Å:10.6 Å:8.5 Å 1:1/2:1/3:1/4:1/5) in the small-angle range and the absence of any distinct diffraction peak in the wide-angle range.

TEST EXAMPLE 2

5% by weight based on the total of the following liquid paraffin and the following water of the monocholesteryl n-hexadecenylsuccinate synthesized in Example 1 as the emulsifier was dissolved in 30 g of liquid paraffin. 70 g of water was added to the resultant solution under stirring to form an emulsion at 70° C. The water-in-oil emulsion thus obtained was left to stand at room temperature for one week to observe the state of phase separation. For comparison, the same procedure as that described above was repeated except that cholesteryl isostearate was used as the emulsifier. The results are given in Table 9.

TABLE 9

| Emulsifier | State of phase |
| --- | --- |
| Monocholesteryl n-hexadecenylsuccinate | no separation |
| Cholesteryl isostearate | complete separation into 2 phases |

It is apparent from the above test results that the monocholesteryl n-hexadecenylsuccinate of the present invention had an emulsifying power higher than that of cholesteryl isostearate.

EXAMPLE A

An emulsified cosmetic of oil-in-water type (dermatologic external preparation containing the sterol derivative of the present invention, invention product 1) was prepared by blending the monocholesteryl n-octadecenylsuccinate synthesized in Example 2 with a bovine brain ceramide (a product of Funakoshi Pharmaceutical Co., Ltd.) which was a mixture of compounds represented by the general formula (1) as shown in Table 11. For comparison, an emulsified cosmetic of oil-in-water type (dermatologic external preparation containing a comparative, comparative product 1) prepared by blending cholesteryl isostearate synthesized by a known process (see U.S. Pat. No. 4,309,448/1982) as shown in Table 11 as used. The skin conductance and chaps were tested by a method which will be described below. The results are given in Table 11.

<Test method>
Ten female subjects of an age of 20 to 50 who suffered from the chapped cheeks in winter were subjected to the test. Samples of different kinds were applied to the left and right cheek skins, respectively, of them once a day for two weeks. One day after the completion of the two-week application, the following tests were conducted:

(1) skin conductance:
The subjects washed their faces with warm water (37° C.) and then rested in a room kept at a temperature of 20° C. and a humidity of 40% for 20 min. Thereafter, the water content of the corneal layer of each of them was determined with a skin conductance meter (manufactured by IBS). A lower conductance value means a more chapped skin and a conductance value of 5 or below indicates serious chaps of the skin. On the contrary, a conductance value of 20 or above indicates that the chaps of the skin are scarcely recognizable.

(2) Score of chaps:
The chaps of the skin was macroscopically observed and the results were evaluated on the basis of the criteria given in Table 10. The score was given in terms of the average ± standard deviation.

TABLE 10

| Score | Judgement of chaps |
| --- | --- |
| 0 | no chaps |
| 1 | slight chaps |
| 2 | more or less chaps |
| 3 | slightly serious chaps |
| 4 | serious chaps |

TABLE 11

| | | Invention product 1 | Comparative product 1 |
| --- | --- | --- | --- |
| Compsn. (wt. %) | arginine monocetyl phosphate | 1.0 | 1.0 |
| | polyoxyethylene(60)-hardened castor oil | 1.0 | 1.0 |
| | bovine brain ceramide [a mixture of compounds of the formula (1)] | 5.0 | 5.0 |
| | monocholesteryl n-octadecenylsuccinate | 5.0 | — |
| | cholesteryl isostearate | — | 5.0 |
| | stearic acid | 1.0 | 1.0 |
| | squalane | 20.0 | 20.0 |
| | vaseline | 4.0 | 4.0 |
| | water | balance | balance |
| Evaluation result | skin conductance | 50 ± 3.5 | 16 ± 2.1 |
| | score of chaps | 0.7 ± 0.3 | 1.4 ± 0.5 |

It is apparent from the above test results that the external preparation for the skin which contained the monocholesteryl n-octadecenylsuccinate of the present invention had a superior effect of remedying the chaps of the skin to that of the preparation containing cholesteryl isostearate.

EXAMPLE B

In the following Examples, compound (2a) refers to N-(2-hydroxy-3-hexadecylpropyl)-N-2-hydroxyethyl-hexadecanamide [$R^c=C_{16}H_{33}$, $R^d=C_{15}H_{31}$ in the general formula (2)] prepared in accordance with the method described in Refcrential Example 1 of Japanese Patent Publication-A No. 192703/1988 (Aug. 10, 1988).

(1) Preparation of mixture of components (A) and (B):
The compound (2a) and cholesteryl hemisuccinate [$R^{10}$ in the general formula (VII) represents —(CH$_2$-)$_2$—] were weighed into a sample vial having a screw glass opening in such a manner as to give 50% by weight of the compound (2a) and 50% by weight of cholesteryl hemisuccinate. The sample vial was heated to 150° C. by using, for example, a heating block. When the compound (2a) and cholesteryl hemisuccinate were completely melted by heating, the heating was ceased and the product was allowed to cool in the atmosphere to obtain a pasty mixture.

(2) Preparation of dermatologic external preparations and evaluation thereof

Use was made of a dermatologic external preparation (invention product 2) prepared by blending vaseline with the mixture obtained in the above (1) in such a manner as to give 1.5% by weight of the compound (2a) and 154 by weight of the cholesteryl hemisuccinate, another dermatologic external preparation (comparative product 2) prepared by blending vaseline with the compound (2a) and cholesterol in such a manner as to give 15% by weight of the compound (2a) and 15% by weight of the cholesterol, and vaseline (comparative product 3) to evaluate skill conductance and score of chaps by the above-described methods (see Example A). Table 12 shows the results.

TABLE 12

|  | Skin conductance | Score of chaps |
| --- | --- | --- |
| Invention product 2 | 60 ± 4.0 | 0.3 ± 0.2 |
| Comparative product 2 | 30 ± 4.0 | 1.0 ± 0.2 |
| Comparative product 3 | 6 ± 0.9 | 2.8 ± 0.7 |

EXAMPLE C

Oil-in-water emulsion cosmetics were produced by blending the compound (2a), cholesteryl hemisuccinate [$R^{10}$ in the general formula (VII) represents —($CH_2$)$_2$—] and cholesteryl lsostearate in proportions specified in Table 13 to evaluate the skin conductance and score of chaps by the same methods as those described in Example A. Table 14 shows the results.

TABLE 13

| | Emulsion cosmetic (unit: % by wt.) | | |
| --- | --- | --- | --- |
| Composition | Invention product 3 | Comparative product 4 | Comparative product 5 |
| arginine monocetyl-phosphate | 1.0 | 1.0 | 1.0 |
| polyoxyethylene (60)/hardened castor oil adduct | 1.0 | 1.0 | 1.0 |
| octyldodecyl myristate | 15.0 | 15.0 | 15.0 |
| squalane | 15.0 | 15.0 | 15.0 |
| stearic acid | 2.0 | 2.0 | 2.0 |
| compound (2a) | 3.0 | 3.0 | 3.0 |
| cholesteryl hemi-succinate | 5.0 | — | — |
| cholesteryl iso-stearate | — | — | 5.0 |
| water | balance | balance | balance |

TABLE 14

|  | Skin conductance | Score of chaps |
| --- | --- | --- |
| Invention product 3 | 45 ± 4.0 | 0.6 ± 0.2 |
| Comparative product 4 | 11 ± 1.0 | 1.5 ± 0.5 |
| Comparative product 5 | 18 ± 2.0 | 1.2 ± 0.3 |

EXAMPLE D

Oil-in-water emulsion cosmetics (invention product 4 and comparative product 6) were produced by blending a ceramide which was a mixture of compounds represented by the general formula (1) [bovine brain ceramide, mfd. by Funakoshi Yakuhin K.K.)], cholesteryl alkenylsuccinate [a mixture of compounds represented by the general formulas (IX) and (X) wherein $R^{11}$=$C_{18}H_{35}$], etc., in proportions specified in Table 15 to evaluate the skin conductance and score of chaps by the same methods as those described in Example A. Table 16 shows the results.

TABLE 15

| | Emulsion cosmetic (unit: % by wt.) | |
| --- | --- | --- |
| Composition | Invention product 4 | Comparative product 6 |
| arginine monocetylphosphate | 1.0 | 1.0 |
| polyoxyethylene (60)/hardened castor oil adduct | 1.0 | 1.0 |
| squalane | 20.0 | 20.0 |
| stearic acid | 1.0 | 1.0 |
| cholesteryl alkenylsuccinate | 5.0 | — |
| ceramide | 5.0 | 5.0 |
| vaseline | 4.0 | 4.0 |
| water | balance | balance |

TABLE 16

|  | Skin conductance | Score of chaps |
| --- | --- | --- |
| Invention product 4 | 50 ± 3.5 | 0.7 ± 0.3 |
| Comparative product 6 | 11 ± 2.0 | 1.4 ± 0.4 |

EXAMPLE E

Dermatologic external preparation (oily ointment)

| <Composition> | % by wt. |
| --- | --- |
| (1) vaseline | 30.0 |
| (2) ceramide [bovine brain ceramide mfd. by Funakoshi Yakuhin K.K.] | 10.0 |
| (3) cholesteryl alkenylsuccinate [a mixture of compounds represented by the general formulas (IX) and (X) wherein $R^{11}$ = $C_{16}H_{31}$] | 10.0 |
| (4) cholesteryl isostearate | 2.0 |
| (5) stearic acid | 4.0 |
| (6) olive oil | q.s. ad 100 |
| (7) l-menthol | 0.3 |
| (8) camphor | 0.3. |

<Production process>

A mixture obtained by mixing the components (1), (7) and (8) and heating and melting them was added to another mixture obtained by mixing the components (2) to (6) and heating and melting them, and the resulting mixture was homogeneously mixed. Then, the mixture thus obtained was cooled to around room temperature to prepare an oily ointment.

EXAMPLE F

Cosmetic (emulsion)

| <Composition> | % by wt. |
| --- | --- |
| oily phase components: | |
| macadamia nut oil | 2.0 |
| squalane | 5.0 |
| cholesteryl alkenylsuccinate [a mixture of compounds represented by the general formulas (IX) and (X) wherein $R^{11}$ = $C_{12}H_{23}$] | 1.0 |
| compound (2a) | 1.0 |
| soybean phospholipid | 0.5 |
| glucocerebroside [bovine brain extract] | 0.5 |
| sorbitan monostearate | 0.5 |
| P.O.E. (60)/hardened castor oil adduct | 1.0 |

| <Composition> | % by wt. |
|---|---|
| aqueous phase components: | |
| glycerol | 1.0 |
| propylene glycol | 1.0 |
| methylparaben | 0.3 |
| perfume | 0.1 |
| purified water | q.s. ad 100 |

<Production process>

The oily phase components were mixed together, melted by heating and then maintained at 70° C. Similarly, the aqueous phase components were mixed together by heating to 70° C. The oily phase mixture was added to the aqueous phase mixture and the resultant mixture was emulsified on an emulsifier. The obtained emulsion was cooled to a final temperature of 30° C. on a heat exchanger and then packed in a container to thereby give an emulsion.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A sterol derivative represented by the following general formulas (I) or (II):

(I)

wherein
R$^1$ represents a residue remaining after removing the hydrogen atom from the hydroxyl group of a natural sterol having one hydroxyl group selected from the group consisting of cholesterol, stigmasterol, sitosterol, lanosterol and ergosterol or a hydrogenation product thereof, R$^2$ represents a group of the formulas:

(in which R$^3$ represents a straight-chain or branched alkenyl or alkyl group having 6 to 20 carbon atoms), and M represents a hydrogen atom, alkali metal, ammonium, alkanolammonium having 2 to 9 carbon atoms in total, alkylammonium or alkenylammonium having 1 to 22 carbon atoms in total, pyridinium substituted by an alkyl or alkenyl group having 1 to 18 carbon atoms, or a basic amino acid, and (II)

wherein
R$^1$ represents a residue remaining after removing the hydrogen atom from the hydroxyl group of a natural sterol having one hydroxyl group or a hydrogenation product thereof, R$^2$ represents a group of the formulas:

(in which R$^3$ represents a straight-chain or branched alkenyl or alkyl group having 6 to 20 carbon atoms), and L represents an alkaline earth metal.

2. The sterol derivative according to claim 1, wherein R$^1$ and R$^3$ in the general formulas (I) and (II) represent a residue remaining after removing the hydrogen atom from the hydroxyl group of the cholesterol and a straight-chain alkenyl or alkyl group having (6 to 20 carbon atoms, respectively.

3. A sterol derivative represented by the following general formula (III):

(III)

wherein
R$^4$ represents a residue remaining after removing the hydrogen atom from the hydroxyl group of a natural sterol having one hydroxyl group selected from the group consisting of cholesterol, stigmasterol, sitosterol, lanosterol and ergosterol, and R$^5$ represents a group of the formula:

(in which R$^6$ represents a straight-chain or branched alkenyl or alkyl group having 6 to 18 carbon atoms).

4. A mixture of two sterol derivatives as set forth in claim 1, wherein the two sterol derivatives are different from each other with respect to only R$^2$, and one has a group of the formula:

(in which R$^3$ represents a straight-chain or branched alkenyl or alkyl group having 6 to 20 carbon atoms) as R$^2$, and another has a group of the formula:

(in which R$^3$ represents a straight-chain or branched alkenyl or alkyl group having 6 to 20 carbon atoms) as R$^2$.

5. A mixture of two sterol derivatives represented by the following general formula (IV):

(IV)

wherein
R$^4$ represents a residue remaining after removing the hydrogen atom from the hydroxyl group of a natural sterol having one hydroxyl group selected from the group consisting of cholesterol, stigmasterol, sitosterol, lanosterol and ergosterol, and

R⁷ represents a group of the formulas:

(in which R⁶ represents a straight-chain or branched alkenyl or alkyl group having 6 to 18 carbon atoms), with the proviso that the two sterol derivatives are different from each other with respect to only R⁷, and that one has a group of the formula:

(in which R⁶ represents a straight-chain or branched alkenyl or alkyl group having 6 to 18 carbon atoms) as R⁷ and another has a group of the formula:

(in which R⁶ represents a straight-chain or branched alkenyl or alkyl group having 6 to 18 carbon atoms) as R⁷.

6. A process for producing the sterol derivative as set forth in claim 1, which comprises reacting a natural sterol having one hydroxyl group selected from the group consisting of cholesterol, stigmasterol, sitosterol, lanosterol and ergosterol or a hydrogenation product thereof, with an alkenylsuccinic anhydride or an alkylsuccinic anhydride.

7. A process for producing the mixture of two sterol derivatives as set forth in claim 4, which comprises reacting a natural sterol having one hydroxyl group or a hydrogenation product thereof with an alkenylsuccinic anhydride or an alkylsuccinic anhydride.

8. The process according to claim 7, wherein the reaction is conducted in the presence of an organic solvent substantially free from water and alcohols.

9. The process according to claim 7, wherein the reaction is conducted in the presence of a reaction catalyst.

10. The process according to claim 7, wherein the reaction is conducted in the presence of an acidic substance as the reaction catalyst.

11. The process according to claim 7, wherein the neutralization/counter ion exchange step is conducted after the reaction.

12. A dermatologic external preparation comprising the following components (A) and (B):

(A) one or more compounds selected from the group consisting of ceramides represented by the following general formula (1) and structural analogs of ceramides represented by the following general formula (2):

wherein Rᵃ and Rᵇ each represent a straight-chain or branched, saturated or unsaturated hydrocarbon group having 8 to 26 carbon atoms which may be optionally substituted by one or more hydroxyl groups, and wherein Rᶜ represents a straight-chain or branched, saturated or unsaturated hydrocarbon group having 10 to 26 carbon atoms, and Rᵈ represents a straight-chain or branched, saturated or unsaturated hydrocarbon group having 9 to 25 carbon atoms, and

(B) one or more sterol derivatives represented by the following general formulas (V) or (VI):

wherein

R¹ represents a residue remaining after removing the hydrogen atom from the hydroxyl group of a natural sterol having one hydroxyl group selected from the group consisting of cholesterol, stigmasterol, sitosterol, lanosterol and ergosterol or a hydrogenation product thereof, R⁸ represents a group of the formulas: —(CH₂)$_n$— (in which n is an integer of 2 to 10), —CH=CH—, (in which R⁹ represents a straight-chain or branched alkenyl or alkyl group having 3 to 20 carbon atoms), and

M represents a hydrogen atom, alkali metal, ammonium, alkanolammonium having 2 to 9 carbon atoms in total, alkylammonium or alkenylammonium having 1 to 22 carbon atoms in total, pyridinium substituted by an alkyl or alkenyl group having 1 to 18 carbon atoms, or a basic amino acid, and wherein R¹ represents a residue remaining after removing the hydrogen atom from the hydroxyl group of a natural sterol having one hydroxyl group selected from the group consisting of cholesterol, stigmasterol, sitosterol, lanosterol and ergosterol or a hydrogenation product thereof, R⁸ represents a group of the formulas: —(CH₂)$_n$— (in which n is an integer of 2 to 10), —CH=CH—, (in which R⁹ represents a straight-chain or branched alkenyl or alkyl group having 3 to 20 carbon atoms), and L represents an alkaline earth metal.

13. The dermatologic external preparation according to claim 12, wherein the said component (B) is one member selected from the group consisting of the sterol derivatives of formulae (V) and (VI), wherein $R^9$ has 6 to 20 carbon atoms.

14. The dermatologic external preparation according to claim 12, wherein the component (B) is one member selected from the group consisting of sterol derivatives represented by the following general formula (VII):

$$R^4-\overset{O}{\underset{\|}{C}}-R^{10}-\overset{O}{\underset{\|}{C}}-OH \quad \text{(VII)}$$

wherein
$R^4$ represents a residue remaining after removing the hydrogen atom from the hydroxyl group of a natural sterol having one hydroxyl group selected from the group consisting of cholesterol, stigmasterol, sitosterol, lanosterol and ergosterol, and $R^{10}$ represents a group of the formulas: $-(CH_2)_n-$ (in which n is an integer of 2 to 10), $-CH=CH-$ or $$-CH-CH_2- \\ \phantom{-}|\phantom{-CH_2} \\ R^{11}$$

(in which $R^{11}$ represents a straight-chain or branched alkenyl or alkyl group having 3 to 18 carbon atoms).

15. The dermatologic external preparation according to claim 12, wherein the component (B) is one member selected from the group consisting of sterol derivatives represented by the following general formula (VIII):

$$R^4-\overset{O}{\underset{\|}{C}}-R^{12}-\overset{O}{\underset{\|}{C}}-OH \quad \text{(VIII)}$$

wherein
$R^4$ represents a residue remaining after removing the hydrogen atom from the hydroxyl group of a natural sterol having one hydroxyl group selected from the group consisting of cholesterol, stigmasterol, sitosterol, lanosterol and ergosterol, and $R^{12}$ represents a group of the formulas: $-(CH_2)_n-$ (in which n is an integer of 2 to 10) or $-CH=CH-$, and a mixture of two sterol derivatives represented by the following general formulas (IX) and (X):

$$R^4-\overset{O}{\underset{\|}{C}}-\overset{R^{11}}{\underset{|}{CH}}-CH_2-\overset{O}{\underset{\|}{C}}-OH \quad \text{(IX)}$$

and $$R^4-\overset{O}{\underset{\|}{C}}-CH_2-\overset{R^{11}}{\underset{|}{CH}}-\overset{O}{\underset{\|}{C}}-OH \quad \text{(X)}$$

wherein
$R^4$ represents a residue remaining after removing the hydrogen atom from the hydroxyl group of a natural sterol having one hydroxyl group selected from the group consisting of cholesterol, stigmasterol, sitosterol, lanosterol and ergosterol, and $R^{11}$ represents a straight-chain or branched alkenyl or alkyl group having 3 to 18 carbon atoms), with the proviso that $R^4$ in the general formula (IX) and $R^4$ in the general formula (X) are the same and that $R^{11}$ in the general formula (IX) and $R^4$ in the general formula (X) are the same.

16. The dermatologic external preparation according to claim 11, wherein the component (B) is one member selected from the group consisting of the mixture of two sterol derivatives which are different from each other with respect to only $R^2$, and one has a group of the formula:

$$-CH-CH_2- \\ \phantom{-}|\phantom{-CH_2} \\ R^3$$

(in which $R^3$ represents a straight-chain or branched alkenyl or alkyl group having 6 to 20 carbon atoms) as $R^2$, and another has a group of the formula:

$$-CH_2-CH- \\ \phantom{-CH_2-}|\phantom{-} \\ \phantom{-CH_2-}R^3$$

(in which $R^3$ represents a straight-chain or branched alkenyl or alkyl group having 6 to 20 carbon atoms) as $R^2$.

17. The dermatologic external preparation accoring to claim 12, wherein the compositional ratio of the component (A) to the component (B) is from 95:5 to 5:95 by weight.

18. The dermatologic external preparation accoring to claim 12, wherein the dermatologic external preparation is an emulsifiied type and the total amount of the components (A) and (B) ranges from 0.01 to 60% by weight based on the whole preparation.

19. The dermatologic external preparation accoring to claim 12, wherein the dermatologic external preparation is an oily type and the total amount of the components (A) and (B) ranges from 1 to 90% by weight based on the whole preparation.

20. The dermatologic external preparation accoring to claim 12, wherein the dermatologic external preparation is a medicinal one.

21. The dermatologic external preparation accoring to claim 12, wherein the dermatologic external preparation is a cosmetic.

22. The sterol derivative according to claim 1, having the formula:

23. The sterol derivative according to claim 1, having the formula:

24. The sterol derivative according to claim 1, having the formula:

* * * * *